US006579545B2

(12) United States Patent
Zyck et al.

(10) Patent No.: US 6,579,545 B2
(45) Date of Patent: Jun. 17, 2003

(54) COATED CHEWING GUM PRODUCTS CONTAINING AN ANTIGAS AGENT

(75) Inventors: Daniel J. Zyck, North Riverside, IL (US); Michael J. Greenberg, Northbrook, IL (US); David G. Barkalow, Deerfield, IL (US); Scott W. Marske, LaGrange, IL (US); Philip G. Schnell, Downers Grove, IL (US); Philip Mazzone, Griffith, IN (US); John E. Hammond, Crete, IL (US); David L. Witkewitz, Bridgeview, IL (US); Daniel J. Sitler, Woodridge, IL (US); Raynold M. Petrocelli, Chicago, IL (US)

(73) Assignee: WM. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/747,300

(22) Filed: Dec. 22, 2000

(65) Prior Publication Data
US 2002/0119216 A1 Aug. 29, 2002

(51) Int. Cl.$^7$ .............................. S23G 3/30; S61K 9/68
(52) U.S. Cl. .............................. 426/5; 424/48; 424/440
(58) Field of Search .................... 426/3, 5; 424/48, 424/440

(56) References Cited

U.S. PATENT DOCUMENTS

| | | |
|---|---|---|
| 1,298,670 A | 4/1919 | Cramer |
| 1,629,461 A | 5/1927 | Berg et al. |
| 2,892,753 A | 6/1959 | Schmidt et al. |
| 2,990,328 A | 6/1961 | Lincoln |
| 3,011,949 A | 12/1961 | Bilotti |
| 3,029,189 A | 4/1962 | Hardy et al. |
| 3,047,461 A | 7/1962 | Hardy et al. |
| 3,075,884 A | 1/1963 | Bilotti et al. |
| 3,196,172 A | 7/1965 | Wright, Jr. et al. |
| 3,308,022 A | 3/1967 | Cummings et al. |
| 3,498,964 A | 3/1970 | Hayashi |
| 3,554,767 A | 1/1971 | Daum |
| 3,590,057 A | 6/1971 | Suzuki et al. |
| 3,845,217 A | 10/1974 | Ferno et al. |
| 3,877,468 A | 4/1975 | Lichtneckert et al. |
| 3,901,248 A | 8/1975 | Lichtneckert et al. |
| 3,995,064 A | 11/1976 | Ehrgott et al. |
| 4,154,814 A | 5/1979 | Hand et al. |
| 4,238,475 A | 12/1980 | Witzel et al. |
| 4,238,510 A | 12/1980 | Cherukuri et al. |
| 4,250,195 A | 2/1981 | Cherukuri et al. |
| 4,283,408 A | 8/1981 | Hirata et al. |
| 4,317,838 A | 3/1982 | Cherukuri et al. |
| 4,374,858 A | 2/1983 | Glass et al. |
| 4,378,374 A | 3/1983 | Reggio et al. |
| 4,386,063 A | 5/1983 | Boden |
| 4,386,106 A | 5/1983 | Merrit et al. |
| 4,400,372 A | 8/1983 | Muhker et al. |
| 4,446,135 A | 5/1984 | Fountaine |
| 4,452,821 A | 6/1984 | Gergely |
| 4,459,311 A | 7/1984 | DeTora et al. |
| 4,474,749 A | 10/1984 | Kruppa |
| 4,512,968 A | 4/1985 | Komiyama et al. |
| 4,533,556 A | 8/1985 | Piccolo et al. |
| 4,555,407 A | 11/1985 | Kramer et al. |
| 4,563,345 A | 1/1986 | Arrick |
| 4,639,368 A | 1/1987 | Niazi et al. |
| 4,647,450 A | 3/1987 | Peters et al. |
| 4,711,774 A | 12/1987 | Denick, Jr. et al. |
| 4,716,033 A | 12/1987 | Denick, Jr. |
| 4,737,366 A | 4/1988 | Gergely et al. |
| 4,753,800 A | 6/1988 | Mozda |
| 4,753,805 A | 6/1988 | Cherukuri et al. |
| 4,755,389 A | 7/1988 | Jones et al. |
| 4,758,424 A | 7/1988 | Denick, Jr. et al. |
| 4,822,597 A | 4/1989 | Faust et al. |
| 4,822,816 A | 4/1989 | Markham |
| 4,828,820 A | 5/1989 | Glass et al. |
| 4,832,994 A | 5/1989 | Fey |
| 4,835,162 A | 5/1989 | Abood |
| 4,849,227 A | 7/1989 | Cho |
| 4,853,212 A | 8/1989 | Faust et al. |
| 4,867,989 A | 9/1989 | Silva et al. |
| 4,882,152 A | 11/1989 | Yang et al. |
| 4,894,234 A | 1/1990 | Sharma et al. |
| 4,908,211 A | 3/1990 | Paz |
| 4,908,212 A | 3/1990 | Kwon et al. |
| 4,929,447 A | 5/1990 | Yang |
| 4,929,508 A | 5/1990 | Sharma et al. |

(List continued on next page.)

FOREIGN PATENT DOCUMENTS

| | | |
|---|---|---|
| DE | 43 42 568 | 6/1984 |
| EP | 0 202 819 A2 | 11/1986 |
| EP | 0 217 109 A2 | 4/1987 |

(List continued on next page.)

OTHER PUBLICATIONS

Beckett, A. H. et al., "Buccal absorption of basis drugs and its application as an in vivo model of passive drug transfer through lipid membranes", *J. Pharm. Pharmac., 19 Suppl*, 1967, pp 31S–41S.

David S. Weinberg et al. "Sublingual absorption of selected opioid analgesics", *Clin. Pharmacol Ther.*, 1998, vol. 44, pp. 335–342.

U.S. patent application Ser. No. 09/286,818, filed Apr. 6, 1999.

U.S. patent application Ser. No. 09/421,905, filed Oct. 20, 1999.

(List continued on next page.)

*Primary Examiner*—Arthur L. Corbin
(74) *Attorney, Agent, or Firm*—Steven P. Shurtz; Brinks Hofer Gilson & Lione

(57) ABSTRACT

A method of making coated chewing gum products containing an antigas agent comprises the steps of providing chewing gum cores; providing a coating comprising a bulk sweetener; providing an antigas agent; and applying the antigas agent and coating syrup to the cores and drying the syrup to produce a coating on the cores.

33 Claims, No Drawings

U.S. PATENT DOCUMENTS

| | | |
|---|---|---|
| 4,933,184 A | 6/1990 | Tsuk |
| 4,935,242 A | 6/1990 | Sharma et al. |
| 4,938,963 A | 7/1990 | Parnell |
| 4,944,949 A | 7/1990 | Story et al. |
| 4,963,369 A | 10/1990 | Song et al. |
| 4,968,511 A | 11/1990 | D'Amelia et al. |
| 4,968,716 A | 11/1990 | Markham |
| 4,971,079 A | 11/1990 | Talapin et al. |
| 4,971,787 A | 11/1990 | Cherukuri et al. |
| 4,975,270 A | 12/1990 | Kehoe |
| 4,978,537 A | 12/1990 | Song |
| 4,997,659 A | 3/1991 | Yatka et al. |
| 5,013,716 A | 5/1991 | Cherukuri et al. |
| 5,015,464 A | 5/1991 | Strobridge |
| 5,045,325 A | 9/1991 | Lesko et al. |
| 5,070,085 A | 12/1991 | Markham |
| 5,110,608 A | 5/1992 | Cherukuri |
| 5,124,156 A | 6/1992 | Shibata et al. |
| 5,126,151 A | 6/1992 | Bodor et al. |
| 5,139,787 A | 8/1992 | Broderick et al. |
| 5,139,794 A | 8/1992 | Patel et al. |
| 5,154,927 A | 10/1992 | Song et al. |
| 5,156,842 A | 10/1992 | Mulligan |
| 5,179,122 A | 1/1993 | Greene et al. |
| 5,182,099 A | 1/1993 | Jonsson et al. |
| 5,229,137 A | 7/1993 | Wolfe |
| 5,244,670 A | 9/1993 | Upson et al. |
| 5,284,657 A | 2/1994 | Lu et al. |
| 5,286,500 A | 2/1994 | Synosky et al. |
| 5,294,433 A | 3/1994 | Singer et al. |
| 5,294,449 A | 3/1994 | Greenberg |
| 5,340,566 A | 8/1994 | Curtis et al. |
| 5,378,131 A | 1/1995 | Greenberg |
| 5,380,530 A | 1/1995 | Hill |
| 5,380,535 A | 1/1995 | Geyer et al. |
| 5,397,580 A | 3/1995 | Song et al. |
| 5,410,028 A | 4/1995 | Asami et al. |
| 5,419,919 A | 5/1995 | Song et al. |
| 5,433,960 A | 7/1995 | Meyers |
| 5,445,834 A | 8/1995 | Burger et al. |
| 5,455,286 A | 10/1995 | Amidon et al. |
| 5,456,677 A | 10/1995 | Spector |
| 5,487,902 A | 1/1996 | Andersen et al. |
| 5,488,962 A | 2/1996 | Perfetti |
| 5,494,685 A | 2/1996 | Tyrpin et al. |
| 5,496,541 A | 3/1996 | Cutler |
| 5,512,306 A | 4/1996 | Carlsson et al. |
| 5,523,097 A | 6/1996 | Song et al. |
| 5,534,272 A | 7/1996 | Bernstein |
| 5,536,511 A | 7/1996 | Yatka |
| 5,543,160 A | 8/1996 | Song et al. |
| 5,554,380 A | 9/1996 | Cuca et al. |
| 5,569,477 A | 10/1996 | Nesbitt |
| 5,571,528 A | 11/1996 | Lee et al. |
| 5,571,543 A | 11/1996 | Song et al. |
| 5,576,344 A | 11/1996 | Sandler et al. |
| 5,580,590 A | 12/1996 | Hartman |
| 5,582,855 A | 12/1996 | Cherukuri et al. |
| 5,585,110 A | 12/1996 | Kalili et al. |
| 5,593,685 A | 1/1997 | Bye et al. |
| 5,601,858 A | 2/1997 | Manshukhani |
| 5,605,698 A | 2/1997 | Ueno |
| 5,607,697 A | 3/1997 | Alkire et al. |
| 5,618,517 A | 4/1997 | Miskewitz |
| 5,628,986 A | 5/1997 | Sanker et al. |
| 5,629,013 A | 5/1997 | Davis |
| 5,629,026 A | 5/1997 | Davis |
| 5,629,035 A | 5/1997 | Miskewitz |
| 5,645,853 A | 7/1997 | Winston et al. |
| 5,651,987 A | 7/1997 | Fuisz |
| 5,656,652 A | 8/1997 | Davis |
| 5,665,386 A | 9/1997 | Bebet et al. |
| 5,665,406 A | 9/1997 | Reed et al. |
| 5,667,802 A | 9/1997 | Grimberg |
| 5,693,334 A | 12/1997 | Miskewitz |
| 5,698,215 A | 12/1997 | Kalili et al. |
| 5,702,687 A | 12/1997 | Miskewitz |
| 5,711,961 A | 1/1998 | Kalili et al. |
| 5,716,928 A | 2/1998 | Benet et al. |
| 5,736,175 A | 4/1998 | Cea et al. |
| 5,744,164 A | 4/1998 | Chauffard et al. |
| 5,753,255 A | 5/1998 | Chavkin et al. |
| 5,756,074 A | 5/1998 | Ascione et al. |
| 5,800,847 A | 9/1998 | Song et al. |
| 5,824,291 A | 10/1998 | Howard |
| 5,834,002 A | 11/1998 | Athanikar |
| 5,846,557 A | 12/1998 | Eisenstadt et al. |
| 5,854,267 A | 12/1998 | Berlin et al. |
| 5,858,383 A | 1/1999 | Precopio |
| 5,858,412 A | 1/1999 | Staniforth et al. |
| 5,858,413 A | 1/1999 | Jettka et al. |
| 5,858,423 A | 1/1999 | Yajima et al. |
| 5,866,179 A | 2/1999 | Testa |
| 5,877,173 A | 3/1999 | Olney et al. |
| 5,882,702 A | 3/1999 | Abdel-Malik et al. |
| 5,889,028 A | 3/1999 | Sandborn et al. |
| 5,889,029 A | 3/1999 | Rolf |
| 5,897,891 A | 4/1999 | Godfrey |
| 5,900,230 A | 5/1999 | Cutler |
| 5,912,007 A | 6/1999 | Pan et al. |
| 5,912,030 A | 6/1999 | Huziinec et al. |
| 5,916,606 A | 6/1999 | Record et al. |
| 5,922,346 A | 7/1999 | Hersh |
| 5,922,347 A | 7/1999 | Häusler et al. |
| 5,928,664 A | 7/1999 | Yang et al. |
| 5,958,380 A | 9/1999 | Winston et al. |
| 5,958,472 A | 9/1999 | Robinson et al. |
| 5,980,955 A | 11/1999 | Grennberg et al. |
| 5,989,588 A | 11/1999 | Korn et al. |
| 6,024,988 A | 2/2000 | Ream et al. |
| 6,066,342 A | 5/2000 | Gurol et al. |
| 6,077,524 A | 6/2000 | Bolder et al. |
| 6,090,412 A | 7/2000 | Hashimoto et al. |
| 6,165,516 A | 12/2000 | Gudas et al. |
| 6,221,402 B1 | 2/2001 | Itoh et al. |
| 6,200,604 B1 | 3/2001 | Pather et al. |
| 6,258,376 B1 | 7/2001 | Athanikar |
| 6,290,985 B2 | 9/2001 | Ream et al. |
| 6,303,159 B2 | 10/2001 | Barkalow et al. |
| 6,322,806 B1 | 11/2001 | Ream et al. |
| 6,350,480 B1 | 2/2002 | Urnezis et al. |
| 6,355,265 B1 | 3/2002 | Ream et al. |
| 2001/0036445 A1 | 11/2001 | Anthanikar |
| 2002/0012633 A1 | 1/2002 | Gmunder et al. |
| 2002/0022057 A1 | 2/2002 | Battery et al. ............... 424/490 |

FOREIGN PATENT DOCUMENTS

| | | |
|---|---|---|
| EP | 0 221 850 A2 | 5/1987 |
| EP | 0 239 541 A2 | 9/1987 |
| EP | 0 371 584 A2 | 6/1990 |
| EP | 0 273 809 B1 | 7/1998 |
| FR | 2 345 938 | 10/1977 |
| FR | 2 635 441 | 2/1990 |
| FR | 2 706 771 | 6/1993 |
| GB | 0 934 596 | 8/1963 |
| GB | 0 963 518 | 7/1964 |
| GB | 1 489 832 | 10/1977 |
| GB | 2 181 646 A | 4/1987 |
| IT | 02/73487 | 7/1997 |
| IT | 01293655 | 3/1999 |
| JP | 91-112450 | 5/1991 |

| | | |
|---|---|---|
| JP | 91-251533 | 11/1991 |
| JP | 94-303911 | 11/1994 |
| JP | 96-19370 | 1/1996 |
| JP | 86/242561 | 10/1996 |
| KR | 94-2868 | 4/1994 |
| WO | WO 84/02271 | 6/1984 |
| WO | WO 90/12511 | 11/1990 |
| WO | WO 90/12583 | 11/1990 |
| WO | WO 92/06680 | 4/1992 |
| WO | WO 95/00038 | 1/1995 |
| WO | WO 95/00039 | 1/1995 |
| WO | WO 95/10290 | 4/1995 |
| WO | WO 96/00070 | 1/1996 |
| WO | WO 96/03975 | 2/1996 |
| WO | WO 97/21424 | 6/1997 |
| WO | WO 97/24036 | 6/1997 |
| WO | WO 98/23165 | 6/1998 |
| WO | WO 98/23166 | 6/1998 |
| WO | WO 98/23167 | 6/1998 |
| WO | WO 99/27798 | 6/1999 |
| WO | WO 99/33352 | 7/1999 |
| WO | WO 99/44436 | 9/1999 |
| WO | WO 00/13523 | 3/2000 |
| WO | WO 00/35296 | 6/2000 |
| WO | WO 00/35298 | 6/2000 |
| WO | WO 00/38532 | 7/2000 |
| WO | WO 02/13781 A1 | 2/2002 |

OTHER PUBLICATIONS

U.S. patent application Ser. No. 09/510,878, filed Feb. 23, 2000.
U.S. patent application Ser. No. 09/535,458, filed Mar. 24, 2000.
U.S. patent application Ser. No. 09/592,400, filed Jun. 13, 2000.
U.S. patent application Ser. No. 09/618,808, filed Jul. 18, 2000.
U.S. patent application Ser. No. 09/631,326, filed Aug. 3, 2000.
U.S. patent application Ser. No. 09/671,552, filed Sep. 27, 2000.
U.S. patent application Ser. No. 09/714,571, filed Nov. 16, 2000.
U.S. patent application Ser. No. 09/759,561, filed Jan. 11, 2001.
U.S. patent application Ser. No. 09/759,838, filed Jan. 11, 2001.
U.S. patent application Ser. No. 09/681,935, filed Jun. 28, 2001.
U.S. patent application Ser. No. 09/924,914, filed Aug. 8, 2001.
U.S. patent application Ser. No. 09/955,870, filed Sep. 19, 2001.
U.S. patent application Ser. No. 09/956,445, filed Sep. 19, 2001.
U.S. patent application Ser. No. 09/990,628, filed Nov. 13, 2001.
U.S. patent application Ser. No. 09/992,122, filed Nov. 13, 2001.
U.S. patent application Ser. No. 10/024,631, filed Dec. 17, 2001.
U.S. patent application Ser. No. 10/044,113, filed Jan. 9, 2002.
"Flavor Encapsulation Technologies, Flavor Unit Sweet, Product Management", H&R (undated) (published at least before Nov. 27, 1996), 25 pages.

Dr. Massimo Calanchi and Dr. Sam Ghanta, "Taste–masking of oral formulations", *Eurand International SpA, Pharmaceutical Manufacturing International*, 1996 (5 pages).
The Eurand Group, Brochure (undated) (published at least before Nov. 27, 1996), (16 pages).
Merck Index, 11$^{th}$ Ed., #1635 "Caffeine" (1989), p. 248.
Merck Index, 12$^{th}$ Ed., #2337 "Cimetidine" (1996), p. 383.
Merck Index, 12$^{th}$ Ed., #3264 "Dimethicone" (1996), p. 544.
Merck Index, 12$^{th}$ Ed., #3972 "Famotidine" (1996), p. 667.
Merck Index, 12$^{th}$ Ed., #6758 "Nizatidine" (1996), p. 1143.
Merck Index, 12$^{th}$ Ed., #6977 "Omeprazole" (1996), p. 1174.
Merck Index, 12$^{th}$ Ed., #8272 "Rabeprazole" (1996), p. 1392.
Merck Index, 12$^{th}$ Ed., #8286 "Ranitidine" (1996), p. 1395.
James G. Elliott, "Application of Antioxidant Vitamins in Foods and Beverages" *Food Technology*, (Feb., 1999), pp. 46–48.
C. Curtis Vreeland, "Nutraceuticals Fuel Confectionery Growth" *Candy R&D*, (Mar., 1999), pp. 29, 31–32, 34–35.
Kitty Broihier, R.D., "Foods of Tomorrow, Milking The Nutrition Market", *Food Processing*, (Mar., 1999), pp. 41, 42 and 44.
Kitty Broihier, R.D., "Tea Time For Nutraceuticals, New Black, Green Tea Products Brew Up a Bevy Of Health Benefits", *Food Processing*; (Mar., 1999), pp. 59, 61 and 63.
Andrea Allen, Jack Neff, Lori Dahm and Mary Ellen Kuhn, "Exclusive Guide to Wellness Foods and Nutraceuticals", Food Processing (Special Supplement), (Mar., 1999).
Product package "Aspergum" distributed by Heritage Consumer Products, LLC (on sale prior to Nov. 27, 1995).
Product package "Chew & Sooth Zinc Dietary Supplement Gum" by Gumtech International, Inc., undated but prior to Dec. 22, 2000.
Product package "Dental Care the Baking Soda Gum" distributed by Church & Dwight Co., Inc. (1998).
Product package "BreathAsure Dental Gum" distributed by Breath Asure, Inc. (1998).
Product package "Trident Advantage with Baking Soda" distributed by Warner–Lambert Co. (1998).
Product package "CHOOZ Antacid/Calcium Supplement with Calcium Carbonate" distribute by Heritage Consumer Products Co., undated but prior to Dec. 22, 2000.
Hertiage Consumer Products Co. article from the Internet "Cosmetics and Toiletries, The Heritage Story", printed Jul. 20, 2000, <http://www.cnewsusa.com/Connecticut/14997, html>, 1 page.
The United States Pharmacopeia The National Formulary—"General Information", dated Jan. 1, 1990 pp 1624–1625 and pp 1696–1697.
Gumtech article from the Internet "Customized Solutions For Customer Brands", printed Oct. 18, 2000,<http://www.gum–tech.com/cus–brands.html>, 3 pages.
Product package for Stay Alert Caffeine Supplement Gum, distributed by Amurol Confections Company (first quarter 1998).
Rabeprazole article from the Internet "Rabeprazole: Pharmacokinetics and Safety in the Elderly", printed Sep. 22, 2000,<http://www.mmhc.com/cg/articles/CG9905/Hum–phries.html>, 2 pages.
Brochure for "Minerals Technologies Specialty Minerals", 1998, 19 pages.

Akitoshi et al., Abstract "Acceleration of Transdermal Absorption of Pharmaceuticals by Essential Oils and Organic Solvents," Chem. Abst., 112:125228t, 1990.

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Transporter: A Critical Review of Current Multidrug Resistant Cell Lines, Chimica et Biophysica Acta., 1139:169–183 (1992).

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453–457.

Kronbach, Thomas et al.; "Oxidation of Midazolam and Triazolam by Human Liver Cytochrome P450IIIA4"(1989) *Molec. Pharm.* 36:89–96.

Lalka et al.; "The Hepatic First–Pass Metabolism of Problematic Drugs" (1993) *J. Clin. Pharmacol.* 33:657–669.

Lum et al.; "Clinical Trials of Modulation of Multidrug Resistance. Pharmacokinetic and Pharmacodynamic Considerations" (1993) *Cancer* 72:3502–3514.

Muranishi, Shozo; "Absorption Enhancers" (1990) *Crit. Rev. Ther. Drug Carrier Sys.* 7:1–33.

Somberg et al.; "The Clinical Implications of First–Pass Metabolism: Treatment Strategies for the 1990's" (1993) *J. Clin. Pharmacol.* 33:670–673.

Tam, Yun K.; "Individual Variation in First–Pass Metabolism" (1993) *Clin. Pharmacokinet.* 25:300–328.

Van Hoogdalem et al.; "Intestinal Drug Absorption Enhancement: An Overview" (1989) *Pharmacol. Ther.* 44:407–443.

Warren et al.; "Increased Accumulation of Drugs in Multidrug–Resistant Cell Induced by Liposomes" (1992) *Cancer Research* 52:3241–3245.

Watkins, Paul B.; "The Role of Cytochromes P–450 in Cyclosporine Metabolism" (1990) *J. Am. Acad. Dermacol.* 23:1301–1309.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical–Chemical Properties Shared by Compounds that Modulate Multidrug Resistance in Human Loukemic Cells" (1988) *Molec. Pharmacol.* 33:454–462.

U.S. patent application Ser. No. 09/651,514, filed Aug. 30, 2000.

U.S. patent application Ser. No. 09/552,290, filed Apr. 19, 2000.

U.S. patent application Ser. No. 09/591,256, filed Jun. 9, 2000.

U.S. patent application Ser. No. 09/621,780, filed Jul. 21, 2000.

U.S. patent application Ser. No. 09/621,643, filed Jul. 21, 2000.

U.S. patent application Ser. No. 09/654,464, filed Sep. 1, 2000.

U.S. patent application Ser. No. 09/653,669, filed Sep. 1, 2000.

U.S. patent application Ser. No. 09/748,699, filed Dec. 22, 2000.

U.S. patent application Ser. No. 09/747,323, filed Dec. 22, 2000.

U.S. patent application Ser. No. 09/749,983, filed Dec. 27, 2000.

COATED CHEWING GUM PRODUCTS CONTAINING AN ANTIGAS AGENT

BACKGROUND OF THE INVENTION

The present invention relates to methods for producing coated chewing gum products. More particularly, the invention relates to producing coated chewing gum products containing an antigas agent that is added to the chewing gum coating such that it will have a controlled fast release from chewing gum for maximum effectiveness.

Coated chewing gum products are well known. Many prior art patents disclose chewing gum products coated with sugar sweeteners or polyol sweeteners. U.S. Pat. No. 4,317,838, for example, discloses a method of applying a sugarless coating to chewing gum. The coating may include calcium carbonate as an anti-sticking agent. Synthetic sweeteners, including many different high-intensity sweeteners, are also suggested for use in the coating.

Another area of interest is the use of medicaments in chewing gum. In some instances, it is contemplated that an active medicament that is added to the chewing gum may be readily released. An active medicament may be added to the gum coating, which is a water soluble matrix, such that during the chewing period, the medicament may be released quickly, resulting in a fast release. This would allow a chewing gum coating to be a carrier for an active medicament, specifically an antacid with these fast release characteristics. For example, U.S. Pat. No. 4,867,989 discloses a chewing gum composition coated with an outer shell containing layers of a mineral compound and a coating syrup, but this patent states that the mineral compound must be added separately and not dispersed in the syrup used to make the coating.

Antacids are usually taken on an "as needed" basis to relieve gastrointestinal disturbances mostly due to dietary indiscretions. These antacids are generally insoluble inorganic salts such as calcium carbonate, magnesium carbonate, calcium hydroxide, magnesium hydroxide, or aluminum hydroxide. Antacids readily neutralize acids in the gastrointestinal (GI) tract and are commonly available in or as antacid tablets. Some typical consumer antacid products are: TUMS, which contains calcium carbonate; MILK of MAGNESIA, which contains magnesium hydroxide, and MAALOX PLUS, which contains a combination of aluminum hydroxide and magnesium hydroxide along with simethicone. Some of these antacid products also include an antigas agent called simethicone to eliminate gas buildup in the GI tract. Other consumer products contain only simethicone as the active ingredient, such as MYLANTA GAS, GAS-X, and PHAZYME.

Previously, antacids have been added to chewing gum and in a chewing gum coating, but some products have not been totally consumer acceptable. The large amount of active antacid needed for effectiveness does not lend itself to giving a good tasting product. Also, the presence of sugar in the antacid chewing gum or coated on the chewing gum of some products is not consumer acceptable because sugar causes dental caries.

A sugarless coated chewing gum produced having an antacid in a sorbitol base coating is currently being sold under the trademark CHOOZ®. It has been found that by adding the antacid to a gum coating, the antacid is quickly released from the chewing gum into saliva and into the gastrointestinal (GI) tract. Relief from GI acidity is quickly obtained, but little relief from gas formation is provided. It would be desirable to have not only fast relief, but relief from gas formation. Thus, there is a need for a way to make coated chewing gum products that provide for gas relief, as well as being acceptable to the consumer from taste and other standpoints.

SUMMARY OF THE INVENTION

It has been found that an antigas agent such as simethicone can be provided in a chewing gum coating to provide relief from gas formation, and that the antigas agent is able to act quickly once the gum product is placed in the mouth.

In a first aspect, the invention is a method of making coated chewing gum products containing an antigas agent comprising the steps of: providing chewing gum cores; providing a coating syrup comprising a bulk sweetener; providing an antigas agent; and applying the antigas agent and coating syrup to the cores and drying the syrup to produce a coating on the cores, the coating containing the antigas agent.

In a second aspect, the invention is a coated chewing gum product containing an antigas agent comprising: a chewing gum core and a coating on the core, the coating comprising an antigas agent.

In a third aspect, the invention is a method of delivering an antigas agent to an individual that provides relief in the gastrointestinal tract comprising the steps of: providing chewing gum cores; providing a coating syrup comprising a bulk sweetener; providing simethicone; applying the simethicone and coating syrup to the cores and drying the syrup to produce a coating on the cores, the coating containing from about 5 mg to about 200 mg simethicone; and chewing the coated chewing gum product in the mouth and swallowing the coating, the coating dispersing and dissolving to provide simethicone as an antigas agent in the gastrointestinal tract.

Preferred embodiments of the invention include the addition of a neutralizing antacid in the coating, and may also include an acid blocker such as a histamine $H_2$-receptor antagonists. These agents inhibit or block the secretion of gastric acid by binding to a specific histamine receptor on the parietal (acid secreting) cell membranes located in the stomach. These agents, which may be added to the chewing gum center or to the coating containing the antigas agent, are used for extended relief of gastrointestinal disturbances and extended relief from stomach acidity. Examples of histamine $H_2$-receptor antagonists are cimetidine, ranitidine and its active salt, nizatidine and famotidine, with famotidine being preferred.

The administration of an antigas agent, and preferably a neutralizing antacid as well, that is contained in a chewing gum coating, provides an effective relief from many gastrointestinal disturbances.

It is believed that providing a larger particle size antacid in a chewing gum coating makes it even more effective and longer lasting. Thus, an advantage of a preferred embodiment of the present invention is administering an antacid to an individual that has a larger particle size than is typically administered orally, giving extended relief while still achieving the effect of fast relief.

DETAILED DESCRIPTION OF THE PREFERRED EMBODIMENTS

As used herein, the term "chewing gum" includes bubble gum and all other types of chewing gum. Unless specified otherwise, all percentages are weight percentages.

As mentioned above, products made by the present invention will preferably include an antacid, such as calcium carbonate. The antacid will preferably be included as part of the coating syrup used to prepare a coated chewing gum product. A typical syrup may contain a polyol, suspended calcium carbonate, simethicone, a binding agent, a high-intensity sweetener and a whitener.

In a preferred embodiment of the present invention, the antacid is contained in the coating of chewing gum products, which allows a chewing gum coating to be a carrier for the antacid and the antigas agent (also sometimes referred to as an antiflatulent). Accordingly, as the chewing gum is chewed, the active antacid and antiflatulent in the gum coating is released into the saliva and ingested to give relief from gastrointestinal disturbances in the GI tract.

The preferred antacids are generally carbonate or hydroxide salts of calcium, magnesium, aluminum, or bismuth, and are generally very water insoluble. Other antacids such as sodium bicarbonate, calcium bicarbonate, and other carbonates, silicates, and phosphates may be used in this invention. When these materials are mixed with acids in the GI tract, the acids are readily neutralized to give relief from GI disturbances.

Antiflatulents may be added to an antacid gum coating to be effective antigas materials and eliminate trapped wind. The most common antigas material is dimethicone (dimethyl polysiloxane) and when mixed with silicone dioxide becomes simethicone. Simethicone is also referred to as activated dimethicone. Simethicone is the most common antigas material and may be the only drug approved antiflatulent. However, other antifoaming agents may be used as antigas agents in this invention. As noted previously, simethicone is in other antacid preparations like MYLANTA GAS and GAS-X at a level of 125 mg per tablet. Other preparations like PHAZYME contain simethicone at higher levels, up to 166 mg. The level of simethicone in a coated chewing gum product may be about 5 mg to about 200 mg per piece of coated gum. When used in combination with an antacid, the level of simethicone may be about 20 mg to about 50 mg.

Simethicone may be blended with a carrier and preferably be added as a dry charge material to a gum coating. Simethicone in some situations may act as an anti-tack agent. To prevent any coating problems while applying simethicone as part of a coating, the simethicone may be encapsulated, agglomerated, entrapped or otherwise physically modified so that it will not affect the gum coating process, but will release during chewing and ingestion. Simethicone may also be blended with flavor and applied on the coated gum piece in between applications of coating syrup. Simethicone USP is readily miscible and may be soluble in mint oils at high levels of use. Besides its antigas effect, simethicone used in a gum coating can also improve the smoothness of the coating.

In addition to antacids, acid blockers may also be used in a simethicone-containing products. Examples of acid blockers are histamine $H_2$-receptor antagonists which include cimetidine, used in an over the counter (OTC) preparation called TAGAMET; famotidine, used in an OTC preparation called PEPCID; the hydrochloride salt of ranitidine, used in ZANTAC; and nizatidine, used in AXID. Some other types of acid blockers are called gastric proton pump inhibitors. These include omeprazole, used in PRILOSEC, and rabeprazole. All of these have been used for the treatment of digestive disorders such as gastritis, dyspepsia, gastric hyperacidity, heartburn, gastric oppression and peptic ulcer.

Neutralizing antacids, which are insoluble inorganic salts, are known to neutralize stomach acidity very quickly. As a result, relief from gastrointestinal distress is fast and effective, but does not last long, possibly up to about 30 minutes. The acid blockers, when taken in combination with the antacid, will start to be effective after about 30 minutes, and be most effective after about 3–6 hours, and may last up to about 9–12 hours.

Acid blockers may also be added to a chewing gum coating. If water soluble, the acid blocker may be added to the sugar or polyol syrup and applied throughout the coating process. Water insoluble acid blockers may be dissolved or dispersed in a solvent, possibly flavors, and applied at various times during the coating process. Preferably, an acid blocker may be added as a powder after it has been preblended with a dry charge material. This could allow more control of the level of the acid blocker used in the chewing gum product and may reduce any instability problems of the acid blocker that may be associated with moisture.

The dosage level of acid blocker used in a preferred coated chewing gum product will vary depending on the acid blocker used. In general, the level of acid blocker will be about 1 mg to about 200 mg, either in the gum center or preferably in a gum coating. This level of acid blocker is used in addition to a high level of antacid or calcium carbonate in the preferred gum coating. The level of calcium carbonate in the preferred gum coating will be about 250 to 800 mg in 1 or 2 pieces of gum product having a weight of about 1.5 to 3 grams.

For antacid chewing gum products, calcium carbonate is the most preferred antacid material. This is mostly due to the fact that the most common inert filler in chewing gum base is calcium carbonate. Calcium carbonate, along with talc (magnesium silicate), which is commonly used in bases for gum products that contain food acids to give tartness to flavors, have been used as fillers in gum base and gum products for many years. Chewing gum bases may also contain the other antacids as inert salts.

Chewing gum bases that contain calcium carbonate do not readily release their calcium carbonate during chewing. Since calcium carbonate (or in other cases talc) is very water insoluble, it releases from gum base either very slowly or over very long extended chewing. As a result, this calcium carbonate is not effective as an antacid. Generally, when calcium carbonate is added to a gum formulation separate from the gum base, calcium carbonate becomes intimately mixed with the base during chewing and also releases slowly. However, when calcium carbonate is used in the coating of the chewing gum, it does become quickly available in the oral cavity and is ingested to be an effective antacid.

Generally, suspension coatings with calcium carbonate for an antacid gum may be made with sugar. Sugar with its naturally sweet taste masks some of the off-taste due to the use of high levels of calcium carbonate. With the advent of new coating technologies using less sweet sugarless polyols instead of sugar, the sweet taste of the coating is significantly reduced. In some coatings where xylitol is used, it is sufficiently sweet as a coating, but other polyols such as maltitol, hydrogenated isomaltulose, sorbitol, or erythritol, are not. When the coating contains high levels of calcium carbonate, the polyols generally lack sufficient sweetness to give a good tasting product. As a result, high-intensity sweeteners are preferably added to the coating containing calcium carbonate to give a high-quality, consumer-acceptable product.

For coated antacid chewing gum type products, the high level of calcium carbonate or other antacid in the coating modifies the taste quality and gum texture. The addition of high-intensity sweeteners to the gum coating improves the taste of the finished product. This also occurs in sugarcoated gums as well as polyol coated gums, so aspartame or another high-intensity sweeteners may also be added to sugar coated gums with calcium carbonate or other antacids. If the high-intensity sweeter is subject to degradation, it may preferably be added as part of a different coating syrup from the coating syrup containing the calcium carbonate, as disclosed in U.S. patent application Ser. No. 09/591,256 filled Jun. 9, 2000 pending, hereby incorporated by reference.

Since calcium carbonate is very water insoluble, as are many of the other neutralizing antacids, the reaction rate of the salts with aqueous acids is dependant on the surface area of the neutralizing agent. Neutralizing agents with a large surface area will react faster with acids than those with a small surface area. Many smaller size particles with a combined large surface area neutralize acids faster than fewer large particles with a combined small surface area. However, larger particle sizes of calcium carbonate give longer lasting relief from stomach acidity. When the calcium carbonate particles are suspended in a coating syrup and applied as a gum coating, the particle sizes of calcium carbonate remains essentially the same throughout the process.

Analysis of a precipitated calcium carbonate having a median particle size of about 5 microns was done before and after being applied as a coating. Before coating, the sample was analyzed and found to have a median particle size of 5.1 microns. After preparing the sample of calcium carbonate in a suspension and applying it to a gum pellet for an antacid gum product, the particle size of the calcium carbonate was 4.9 microns.

It has been determined that a calcium carbonate having a median particle size of about 3 microns or greater is sufficient to give longer lasting relief of excess stomach activity. Preferably, the median particle size of the calcium carbonate in the coating will be between about 3 microns and about 75 microns, and more preferably, between about 3 microns and about 15 microns.

In terms of water solubility, larger particles have a tendency to dissolve more slowly in water, and as calcium carbonate dissolves, it neutralizes stomach acidity. Smaller particles of calcium carbonate could react faster, and larger particles would react slower.

In addition to the particle size of calcium carbonate, different crystal structures have an effect on the rate of dissolution and the rate of neutralization. Natural forms of calcium carbonate such as Calcite, Aragonite, and Vaterite are highly crystalline forms of calcium carbonate and could dissolve more slowly to give longer lasting neutralizing effect. Marble, Dolomite, and even Mollusk shells are made of amorphous forms of calcium carbonate, and could dissolve faster and neutralize acidity faster than crystalline forms. Precipitated calcium carbonate, which is purified from natural sources, is a "micro" crystalline form and would dissolve quickly and neutralizes acidity quickly.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises about 10% to about 50% of the gum, and in some preferred embodiments approximately 25% to about 35% by weight, of the chewing gum. In pellet gum center formulations, the level of insoluble gum base may be much higher.

In a preferred embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weights of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weights of about 2,000 to about 90,000, polyisoprene, polyethylene, vinyl acetate-vinyl laurate copolymers having vinyl laurate contents of about 5% to about 50% by weight of the copolymer, and combinations thereof. Preferred ranges are: 50,000 to 80,000 GPC weight average molecular weight for polyisobutylene; 1:1 to 1:3 bound styrene-butadiene for styrene-budadiene; 10,000 to 65,000 GPC weight average molecular weight for polyvinyl acetate, with the higher molecular weight polyvinyl acetates typically used in bubble gum base; and a vinyl laurate content of 10–45% for vinyl acetate-vinyl laurate.

Natural elastomers may include natural rubber such as smoked or liquid latex and guayule, as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water-insoluble gum base portion, a typical chewing gum composition includes a water-soluble bulk portion and one or more flavoring agents. The water-soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High-intensity artificial sweeteners can also be used, alone or in combination, with the above. Preferred sweeteners include, but are not limited to, sucralose, aspartame, N-substituted APM derivatives such as neotame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extrusion may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; oligofructose (Raftilose); inulin (Raftilin); fructooligosaccharides (NutraFlora); palatinose oligosaccharide; guar gum hydrolysate (BeneFiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

In general, chewing gum is manufactured by sequentially adding the various chewing gum ingredients to a commercially available mixer known in the art. After the ingredients have been thoroughly mixed, the gum mass is discharged from the mixer and shaped into the desired form, such as rolling into sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

After the ingredients are mixed, the gum mass is formed into pellets or balls. Pellet or ball gum is prepared as conventional chewing gum but formed into pellets that are pillow shaped, or into balls. The pellets/balls are used as cores for the coated product. The cores can be sugar or polyol coated or panned by conventional panning techniques to make a unique coated pellet gum. The weight of the coating may be about 20% to about 50% of the weight of the finished product, but may be as much as 75% of the total gum product.

Conventional panning procedures generally coat with sucrose, but recent advances in panning have allowed use of other carbohydrate materials to be used in place of sucrose. Some of these materials include, but are not limited to, sugars such as dextrose, maltose, isomaltulose, and tagatose, or sugarless bulk sweeteners such as xylitol, sorbitol, lactitol, hydrogenated isomaltulose, erythritol, maltitol, and other new polyols (also referred to as alditols) or combinations thereof. The coating is preferably sugarless. A preferred coating comprises about 30% to about 75% maltitol. These materials may be blended with panning modifiers including, but not limited to, gum arabic, gum talha, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth. Antitack agents may also be added as panning modifiers, which allow the use of a variety of carbohydrates and sugar alcohols. Flavors may also be added with the sugar or sugarless coating to yield unique product characteristics.

As noted above, the coating may contain ingredients such as flavoring agents, as well as dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent.

High-intensity sweeteners contemplated for use in the coating include but are not limited to synthetic substances, such as saccharin, thaumatin, alitame, saccharin salts, aspartame, N-substituted APM derivatives such as neotame, sucralose, cyclamic acid and its salts, glycyrrhizin, dihydrochalcones, monellin and acesulfame-K or other salts of acesulfame. The high-intensity sweetener may be added to the coating syrup in an amount such that the coating will contain from about 0.01% to about 2.0%, and preferably from about 0.1% to about 1.0% high-intensity sweetener. Preferably the high-intensity sweetener is not encapsulated.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

When high amounts of calcium carbonate or other antacid is used, the calcium carbonate is dispersed or suspended in the coating syrup that contains the sugar or polyol, thus making a syrup suspension. Generally, as the level of calcium carbonate is increased, the level of sugar or polyol is decreased. Levels of calcium carbonate used may be as low as 25% of the total solids or as high as 50% of the total solids in the syrup, and more preferably will comprise about 30% to about 40% of the total solids. In preferred embodiments, the calcium carbonate will comprise about 25% to about 50% of the gum coating, and more preferably about 30% to about 40% of the gum coating.

Coloring agents are preferably added directly to the syrup suspension in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha, guar gum, karaya gum, locust bean gum, alginate gums, xanthan gum, arabinogalactan, various cellulose derivatives, vegetable gums, gelatin and mixtures thereof, with gum arabic being preferred. The binding agent is preferably used at a level of at least about 2% of the coating syrup.

The coating is initially present as a liquid syrup which contains from about 30% to about 80% of the coating ingredients previously described herein, and from about 20% to about 70% of a solvent such as water. In general, the coating process is carried out in a rotating pan. Sugar or sugarless gum center tablets to be coated are placed into the rotating pan to form a moving mass. The material or syrup suspension which will eventually form the coating is applied or distributed over the gum center tablets. Flavoring agents may be added before, during and after applying the syrup suspension to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. (38° C.) to about 240° F. (116° C.). Preferably, the syrup temperature is from about 130° F. (54° C.) to about 200° F. (94° C.) throughout the process in order to prevent the polyol or sugar in the syrup suspension from crystallizing. The syrup suspension may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup suspension. Any number of coats may be applied to the gum center tablet. Preferably, no more than about 75–100 coats are applied to the gum center tablets. The present invention contemplates applying an amount of syrup sufficient to yield a coated comestible containing about 20% to about 75% coating.

Those skilled in the art will recognize that in order to obtain a plurality of coated layers, a plurality of premeasured aliquots of coating syrup suspension may be applied to the gum center tablets. It is contemplated, however, that the volume of aliquots of syrup suspension applied to the gum center tablets may vary throughout the coating procedure.

Once a coating is applied to the gum center tablets, the present invention contemplates drying the wet syrup suspension in an inert medium. A preferred drying medium comprises air. Preferably, forced drying air contacts the wet syrup coating in a temperature range of from about 70° F. (21° C.) to about 115° F. (46° C.). More preferably, the drying air is in the temperature range of from about 80° F. (27° C.) to about 100° F. (38° C.). The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Preferably, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

The present invention also contemplates the application of powder material after applying an aliquot of coating syrup to help build up the coating.

In addition to applying a plurality of liquid layers and drying with air, a dry charge material may be added to dry the coating applications. This is especially useful when coating with some sugars and polyols, such as dextrose, sorbitol, maltitol, and hydrogenated isomaltulose. A liquid addition of coating syrup is made in the coating process and after a specified time to allow the liquid to spread evenly over the pieces, a dry powder material is applied. This also helps to dry the liquid coating. This is referred to as dry charging and is commonly used in "soft" panning operations and is commonly known by those skilled in the art. The dry charge material may consist mostly of the sugar or polyol used in the liquid coating, but may also contain other additives such as gums, dispersing agents, and antitack agents. The simethicone or other antigas agent could be preblended with the dry charge material and applied in about 3 to 12 dry charge applications. After a dry charge application, 2 to 4 liquid applications are made to cover the dry charge material.

When flavors are added to a sugar or sugarless coating of pellet gum to enhance the overall flavor of gum, the flavors are generally preblended with the coating syrup just prior to applying it to the core or added together to the core in one or more coating applications in a revolving pan containing the cores. Simethicone may be pre-blended with the flavor before it is applied to the cores. Generally, the coating syrup is very hot, about 130° F. (54° C.) to 200° F. (93° C.), and the flavor may volatilize if preblended with the coating syrup too early.

The coating syrup is preferably applied to the gum cores as a hot liquid, the sugar or polyol allowed to crystallize, and the coating then dried with warm, dry air. Aliquots of syrups are preferably applied in about 30 to 80 applications to obtain a hard shell coated product having an increased weight gain of about 20% to 75%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors are not used in coatings.

EXAMPLES

The following examples of the invention are provided by way of explanation and illustration.

As noted earlier, the gum formulas can be prepared as sugar or sugarless type formulations and made in a pellet or pillow shape or a round ball or any other shape of product for coating/panning. However, gum formulas for pellet centers are generally adjusted to a higher level of gum base to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 50% gum base with a corresponding decrease in the other ingredients except flavor. Even higher levels of base may be used when calcium carbonate or another antacid is added to a pellet coating. Generally flavor levels in the gum increase with the level of gum base as the base tends to bind flavors into the gum and more flavor is needed to give a good flavorful product. However flavors can also be added to the coating to give increased flavor impact and more flavor perception.

Some typical sugar gum center formulations are shown in Table 1 that can be used as centers that are coated with a coating that contains an antigas agent to give an effective antigas chewing gum product.

TABLE 1

(WEIGHT PERCENT)

| | EX. 1 | EX. 2 | EX. 3 | EX. 4 | EX. 5 | EX. 6 |
|---|---|---|---|---|---|---|
| SUGAR | 48.0 | 48.0 | 46.0 | 40.0 | 39.0 | 36.0 |
| GUM BASE | 30.0 | 35.0 | 40.0 | 30.0 | 35.0 | 40.0 |
| CORN SYRUP | 20.0 | 15.0 | 12.0 | 18.0 | 14.0 | 12.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONOHYDRATE | — | — | — | 10.0 | 10.0 | 10.0 |

Higher levels of base may be used with a corresponding decrease in other ingredients. Also, other sugars may be used in the gum center.

Calcium carbonate can then be used in the coating formula on the various pellet gum formulations. The following Table 2 shows some sugar and dextrose type coating formulas: Using a 1 gram center, the levels of calcium carbonate in the following tables will give 250–800 mg per 1 or 2 pieces in 1.5–3.0 gram pieces with 33% to 66% coating. A 2% level of simethicone in a coating on a 2.25 gram coated gum with a 55.5% coating will give 25 mg of simethicone, which is the amount conventionally found in some antacid preparations. A 2.5% level of simethicone in a 2.0 gram coated gum product with 5% simethicone in the coating will give a product containing 50 mg of simethicone.

TABLE 2

(DRY WEIGHT PERCENT)

| | EX. 7 | EX. 8 | EX. 9 | EX. 10 | EX. 11 | EX. 12 |
|---|---|---|---|---|---|---|
| SUGAR | 69.3 | 59.3 | 51.8 | 66.3 | 63.3 | 49.3 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | 25.0 | 30.0 | 40.0 | 25.0 | 30.0 | 40.0 |
| FLAVOR | 1.0 | 1.5 | 1.0 | 1.5 | 1.5 | 1.5 |
| WAX | 0.1 | 0.1 | 0.1 | 0.1 | 0.1 | 0.1 |
| ACESULFAME K | 0.1 | 0.1 | 0.1 | 0.1 | 0.1 | 0.1 |
| SIMETHICONE* | 2.0 | 5.0 | 2.0 | 5.0 | 2.0 | 5.0 |

| | EX. 13 | EX. 14 | EX. 15 | EX. 16 |
|---|---|---|---|---|
| DEXTROSE MONOHYDRATE | 69.7 | 49.2 | 70.2 | 50.2 |
| GUM ARABIC | 1.5 | 3.0 | 1.5 | 3.0 |
| TITANIUM DIOXIDE | 0.5 | 1.0 | — | — |
| CALCIUM CARBONATE | 25.0 | 40.0 | 25.0 | 40.0 |
| FLAVOR | 1.0 | 1.5 | 1.0 | 1.5 |
| WAX | 0.1 | 0.1 | 0.1 | 0.1 |
| ACESULFAME K | 0.2 | 0.2 | 0.2 | 0.2 |
| SIMETHICONE* | 2.0 | 5.0 | 2.0 | 5.0 |

*Simethicone is preblended with flavor before applying.

The above formulations are made by making a coating syrup by dissolving the sugar or dextrose monohydrate and gum arabic in solution at boiling, and suspending titanium dioxide and/or calcium carbonate in this syrup. Flavor and simethicone is not mixed with hot syrup, but added with one or more coating applications. Acesulfame K may be added as part of the coating syrup. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. Table 3 gives these types of formulations.

TABLE 3

(DRY WEIGHT PERCENT)

|  | EX. 17 | EX. 18 | EX. 19 | EX. 20 | EX. 21 | EX. 22 |
|---|---|---|---|---|---|---|
| SUGAR* | 61.8 | 47.8 | — | — | 51.8 | — |
| DEXTROSE MONOHYDRATE* | — | — | 61.1 | 47.6 | — | 40.1 |
| POWDER SUGAR** | 8.0 | 3.0 | — | — | — | — |
| POWDER DEXTROSE** | — | — | 8.0 | 3.0 | 8.0 | 5.0 |
| GUM ARABIC POWDER** | 2.0 | 3.0 | 2.0 | 3.0 | 8.0 | 6.0 |
| GUM ARABIC SOLUTION | — | — | — | — | 4.0 | 2.0 |
| FLAVOR** | 1.0 | 1.0 | 1.5 | 1.0 | 1.0 | 1.5 |
| WAX | 0.1 | 0.1 | 0.1 | 0.1 | 0.1 | 0.1 |
| CALCIUM CARBONATE | 25.0 | 40.0 | 25.0 | 40.0 | 25.0 | 40.0 |
| ACESULFAME | 0.1 | 0.1 | 0.3 | 0.3 | 0.1 | 0.3 |
| SIMETHICONE** | 2.0 | 5.0 | 2.0 | 5.0 | 2.0 | 5.0 |

*Powder and/or crystalline sugar along with gum arabic may be blended with calcium carbonate, or calcium carbonate may be suspended in the sugar or dextrose syrup.
**Some simethicone is preblend with powder sugar, powder dextrose, or powder gum arabic before use. Other simethicone is mixed with the flavor.

In Examples 17–20, gum arabic is blended in the sugar/dextrose syrup. In Examples 21 and 22, gum arabic powder is dry charged after a gum arabic solution is applied in the first stages of coating, which is then followed by a hard shell coating of sugar solution or dextrose solution.

Gum arabic may also be used in coating of sugarless gum centers. Like sugar gum centers, the base formulation can be increased in proportion to the amount of coating applied to the center. Generally, the base level may be increased to 30–46% with the other ingredients proportionally reduced.

Some typical sugarless gum center formulations are shown in Table 4 that can be used as centers that are coated with calcium carbonate and simethicone to give an effective antigas product.

TABLE 4

(WEIGHT PERCENT)

|  | EX. 23 | EX. 24 | EX. 25 | EX. 26 | EX. 27 | EX. 28 | EX. 29 |
|---|---|---|---|---|---|---|---|
| GUM BASE | 35.0 | 35.0 | 30.0 | 35.0 | 30.0 | 40.0 | 35.8 |
| CALCIUM CARBONATE[b)] | — | — | 5.0 | 15.0 | 10.0 | — | 14.5 |
| SORBITOL | 43.1 | 44.9 | 46.0 | 43.1 | 49.8 | 41.0 | 40.6 |
| MANNITOL | 10.0 | 10.0 | 5.0 | — | — | 8.0 | — |
| GLYCERIN | — | 8.0 | 2.0 | 3.0 | 8.0 | 2.0 | 3.0 |
| SORBITOL LIQUID | 10.0 | — | 10.0 | — | — | 6.0[a)] | 1.05[c)] |
| FLAVOR | 1.5 | 1.5 | 1.5 | 2.5 | 2.0 | 2.0 | 2.5 |
| ENCAPSULATED HIGH-INTENSITY SWEETENER | 0.4 | 0.4 | 0.5 | 1.0 | 0.2 | 0.6 | 2.0 |
| LECITHIN | — | 0.2 | — | 0.4 | — | 0.4 | 0.55 |

[a)]Lycasin brand hydrogenated starch hydrolyzate is used instead of sorbitol liquid.
[b)]This material is base filler and may not release to give an antacid effect.
[c)]Water is added in place of sorbitol liquid.

In the above center formulations, the high-intensity sweetener used is aspartame, acesulfame K, or a combination thereof. However other high-intensity sweeteners such as alitame, salts of acesulfame, cyclamate and its salts, saccharin and its salts, neotame, sucralose, thaumatin, monellin, dihydrochalcones, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high-intensity sweetener.

Simethicone can be used in sugarless coating with xylitol, sorbitol, maltitol, lactitol, hydrogenated isomaltulose and erythritol. Gum arabic acts as a binding agent, film former and hardener of the coated pellet. Using a 1 gram center, the levels of antacid in the following tables will give 250–800 mg of antacid per 1 or 2 pieces in 1.5–3.0 gram chewing gum product pieces with 33% to 66% coating. A 2% level of simethicone in a coating on a 2.25 gram coated gum with a 55.5% coating will give 25 mg of simethicone. A 2.5% level of simethicone in a 2.0 gram coated gum piece with 5% in a coating will give 50 mg of simethicone.

TABLE 5

(DRY WEIGHT PERCENT)

|  | EX. 30 | EX. 31 | EX. 32 | EX. 33 | EX 34 | EX. 35 |
|---|---|---|---|---|---|---|
| XYLITOL | 67.1 | 46.6 | 63.2 | 45.0 | 63.1 | 43.5 |
| GUM ARABIC | 4.0 | 6.0 | 7.0 | 8.5 | 8.5 | 10.0 |
| FLAVOR | 1.0 | 1.0 | 1.0 | 1.0 | 1.0 | 1.0 |
| TITANIUM DIOXIDE | 0.5 | 0.9 | — | — | — | — |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| CALCIUM CARBONATE | 25.0 | 40.0 | 25.0 | 40.0 | 25.0 | 40.0 |
| ACESULFAME K | 0.2 | 0.3 | 0.2 | 0.3 | 0.2 | 0.3 |
| SIMETHICONE** | 2.0 | 5.0 | 2.0 | 5.0 | 2.0 | 5.0 |

*Lake color dispersed in xylitol solution.
**Simethicone may be dissolved or dispersed in flavor.

The above formulas are used to coat pellets by applying a xylitol/gum arabic syrup in multiple coats and air-drying. Color or titanium dioxide is also mixed in the xylitol/gum arabic syrup. Calcium carbonate may be suspended in the xylitol hot syrup or added as a dry powder between syrup applications. The acesulfame K may be mixed into the coating syrup before it is applied. After the pellets have been coated and dried, talc and wax are added to give a polish.

Like xylitol, maltitol coatings may also contain a combination of antacid materials and simethicone. The following formulation can be made.

TABLE 6

(DRY WEIGHT PERCENT)

| | EX. 36 | EX. 37 | EX. 38 | EX. 39 | EX 40 | EX. 41 |
|---|---|---|---|---|---|---|
| MALTITOL | 61.5 | 42.5 | 54.3 | 49.4 | 55.8 | 48.1 |
| MALTITOL POWDER | 5.0 | 10.0 | 7.5 | 5.0 | 10.0 | 6.0 |
| GUM TALHA | 2.0 | 4.0 | 6.0 | 2.0 | 3.0 | 6.0 |
| FLAVOR | 0.5 | 0.4 | 0.7 | 0.5 | 0.3 | 1.0 |
| TITANIUM DIOXIDE | 0.5 | 0.5 | 1.0 | 0.5 | 0.4 | 1.3 |
| TALC | 0.1 | 0.1 | 0.1 | 0.1 | 0.1 | 0.1 |
| WAX | 0.1 | 0.1 | 0.1 | 0.1 | 0.1 | 0.1 |
| CALCIUM CARBONATE* | 25.0 | 40.0 | 25.0 | 40.0 | 25.0 | 35.0 |
| ACESULFAME K | 0.3 | 0.4 | 0.3 | 0.4 | 0.3 | 0.4 |
| SIMETHICONE | 5.0 | 2.0 | 5.0 | 2.0 | 5.0 | 2.0 |

*Calcium carbonate has a median particle size of 5.1 microns.

Although some simethicone may be premixed with flavor, maltitol powder and simethicone are used to dry charge in the early stages of coating. Maltitol, gum talha, calcium carbonate, and titanium dioxide are blended into the coating syrup and applied to the gum pellets. The mixture is applied as a syrup suspension. After all coating is applied and dried, talc and wax are added to give a polish.

In a similar manner, coatings with sorbitol, lactitol and hydrogenated isomaltulose may be made in the coating formulas in Table 6 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum talha could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, magnesium carbonate, starches, gums like arabinogalactan, gum talha, gum arabic or other moisture absorbing materials. Also, powdered sweeteners or flavors could be added with the dry charge.

Polyols such as sorbitol, maltitol, lactitol and hydrogenated isomaltulose are not sufficiently sweet compared to sugar or xylitol, so high-intensity sweeteners are preferably added to the coating. Beside aspartame, other high-intensity sweeteners may also be used such as acesulfame K, salts of acesulfame, cyclamate and its salts, saccharin and its salts, alitame, sucralose, thaumatin, monellin, dihydrochalcones, glycyrrhizin, neotame, and combinations thereof. When adding calcium carbonate or other antacids, and a hot syrup is applied, heat and high pH may degrade some sweeteners, so only stable high-intensity sweeteners should be used if the high-intensity sweetener is added in the main coating syrup.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

What is claimed is:

1. A method of making coated chewing gum products containing an antigas agent comprising the steps of:
   a) providing chewing gum cores;
   b) providing a coating syrup comprising a bulk sweetener;
   c) providing an antigas agent and combining the antigas agent with another ingredient to be used in making the coating to form an antigas ingredient; and
   d) applying the antigas ingredient and the coating syrup separately to the cores, the coating syrup being applied in multiple applications with drying after each application to produce a coating on the cores, the coating thereby containing the antigas agent.

2. The method of claim 1 wherein the bulk sweetener is a polyol.

3. The method of claim 2 wherein the polyol is selected from the group consisting of sorbitol, erythritol, xylitol, maltitol, lactitol, hydrogenated isomaltulose and combinations thereof.

4. The method of claim 1 wherein the antigas agent is simethicone.

5. The method of claim 1 wherein the coating further comprises a neutralizing antacid.

6. The method of claim 5 wherein the neutralizing antacid comprises between about 25% and about 50% of the total solids in the coating syrup.

7. The method of claim 5 wherein the antacid is calcium carbonate and comprises between about 30% and about 40% of the total solids in the coating syrup.

8. The method of claim 5 wherein the neutralizing antacid comprises between about 30% and about 40% of the coating.

9. The method of claim 1 wherein the coating syrup further comprises a binding agent.

10. The method of claim 9 wherein the binding agent is selected from the group consisting of gum arabic, gum talha, guar gum, karaya gum, locust bean gum, alginate gums, xanthan gum, arabinogalactan, cellulose derivatives, vegetable gums, gelatin and mixtures thereof.

11. The method of claim 9 wherein the binding agent comprises at least about 2% of the coating syrup.

12. The method of claim 1 wherein the coating further comprises a high-intensity sweetener.

13. The method of claim 12 wherein the high-intensity sweetener is selected from the group consisting of sucralose, aspartame, N-substituted APM derivatives, salts of acesulfame, alitame, saccharin and its salts, cyclamic acid and its salts, glycyrrhizin, dihydrochalcones, thaumatin, monellin and mixtures thereof.

14. The method of claim 12 wherein the high-intensity sweetener comprises acesulfame K.

15. The method of claim 1 wherein the bulk sweetener comprises maltitol.

16. The method of claim 1 wherein the coating is sugarless.

17. The method of claim 1 wherein a powdered polyol is applied to the cores between applications of the coating syrup.

18. The method of claim 1 wherein the coating further comprises an acid blocker.

19. The method of claim 18 wherein the acid blocker is a histamine H$_2$-receptor antagonist selected from the group consisting of cimetidine, ranitidine and its active salt, famotidine, nizatidine and mixtures thereof.

20. The method of claim 19 wherein the histamine H$_2$-receptor antagonist comprises famotidine.

21. The method of claim 1 wherein the antigas agent is simethicone and the simethicone is combined with said other ingredient to produce physically modified simethicone.

22. The method of claim 21 wherein the simethicone is encapsulated.

23. The method of claim 21 wherein the simethicone is physically modified by being agglomerated.

24. The method of claim 21 wherein the simethicone is physically modified by being entrapped.

25. The method of claim 1 wherein the coating further comprises a flavor, and the flavor constitutes said other ingredient, and the antigas agent and the flavor are preblended and applied to the cores between applications of the coating syrup.

26. The method of claim 1 wherein the other ingredient constitutes a carrier and the antigas agent is blended with said carrier and applied to the cores as a dry charge between applications of the coating syrup.

27. A method of making coated chewing gum products containing an antigas agent comprising the steps of:
 a) providing chewing gum cores;
 b) providing a coating syrup comprising:
  i) a bulk sweetener and
  ii) a neutralizing antacid;
 c) providing a dry charge material comprising a bulk sweetener and simethicone; and
 d) applying the coating syrup and dry charge material to the chewing gum cores to produce a coating on the cores, the coating comprising the simethicone, and the antacid constituting between about 25% and about 60% of the coating.

28. The method of claim 27 wherein the coating comprises about 30% to about 75% maltitol.

29. The method of claim 27 wherein multiple coats of coating syrup and dry charge material are applied to build up the coating.

30. The method of claim 27 wherein the dry charge material and coating syrup both include maltitol as the bulk sweetener.

31. A method of delivering an antigas agent to an individual that provides relief in the gastrointestinal tract comprising the steps of:
 a) providing chewing gum cores;
 b) providing a coating syrup comprising a bulk sweetener;
 c) providing simethicone and combining the simethicone with another ingredient to be used in making the coating to form a simethicone ingredient;
 d) applying the simethicone ingredient and the coating syrup to the cores and drying the syrup to produce a coating on the cores, the simethicone ingredient being applied separately from the syrup, the coating containing from about 5 mg to about 200 mg simethicone; and
 e) chewing the coated chewing gum product in the mouth and swallowing the coating, the coating dispersing and dissolving to provide simethicone as an antigas agent in the gastrointestinal tract.

32. The method of claim 31 wherein the simethicone is combined with said other ingredient to produce physically modified simethicone.

33. The method of claim 32 wherein the simethicone is encapsulated.

* * * * *

UNITED STATES PATENT AND TRADEMARK OFFICE
CERTIFICATE OF CORRECTION

PATENT NO. : 6,579,545 B2
DATED : June 17 2003
INVENTOR(S) : Daniel J. Zyck et al.

It is certified that error appears in the above-identified patent and that said Letters Patent is hereby corrected as shown below:

<u>Title page, Item [54], and Column 1, lines 1-2,</u>
before "COATED CHEWING", insert -- METHOD FOR PREPARING --.
Item [56], References Cited, FOREIGN PATENT DOCUMENTS, delete "02/73487" and substitute -- 02173487 -- in its place.
OTHER PUBLICATIONS, "Cosmetics and Toiletries", reference, immediately after "14997", delete "," (comma) and substitute -- . -- (period) in its place.

Signed and Sealed this

Seventeenth Day of August, 2004

JON W. DUDAS
*Acting Director of the United States Patent and Trademark Office*